(12) United States Patent
Fink

(10) Patent No.: US 9,121,841 B2
(45) Date of Patent: Sep. 1, 2015

(54) PIPETTING ARRANGEMENT AND METHOD OF CONTROLLING A PIPETTING ARRANGEMENT OR OF PRODUCING LIQUID PRODUCT DOSES

(75) Inventor: Pius Fink, Hombrechtikon (CH)

(73) Assignee: Sias AG, Hombrechtikon (CH)

( * ) Notice: Subject to any disclaimer, the term of this patent is extended or adjusted under 35 U.S.C. 154(b) by 182 days.

(21) Appl. No.: 13/697,916

(22) PCT Filed: May 14, 2010

(86) PCT No.: PCT/EP2010/056662
§ 371 (c)(1),
(2), (4) Date: Nov. 14, 2012

(87) PCT Pub. No.: WO2010/084208
PCT Pub. Date: Jul. 29, 2010

(65) Prior Publication Data
US 2013/0056079 A1      Mar. 7, 2013

(51) Int. Cl.
*B01L 3/02* (2006.01)
*G01N 35/10* (2006.01)

(52) U.S. Cl.
CPC ............ *G01N 35/1072* (2013.01); *B01L 3/021* (2013.01); *B01L 2300/0861* (2013.01); *B01L 2400/0487* (2013.01); *Y10T 137/0318* (2015.04)

(58) Field of Classification Search
CPC .............. C12M 1/265; C12M 33/04; B01J 2219/00369; B01L 3/021; A61M 5/31525; G01N 35/1016; G01N 35/1065

USPC .......................................................... 422/509
See application file for complete search history.

(56) References Cited

U.S. PATENT DOCUMENTS

| | | | |
|---|---|---|---|
| 5,364,111 A * | 11/1994 | Wunsch | 277/557 |
| 5,447,691 A * | 9/1995 | Sanuki | 422/509 |
| 7,396,512 B2 | 7/2008 | DiTrolio et al. | |
| 8,656,792 B2 | 2/2014 | Kirste et al. | |
| 2003/0064007 A1* | 4/2003 | Kim et al. | 422/100 |
| 2003/0215957 A1 | 11/2003 | Lemmo et al. | |
| 2009/0155123 A1 | 6/2009 | Williams et al. | |
| 2012/0195811 A1* | 8/2012 | Nelson | 422/522 |

FOREIGN PATENT DOCUMENTS

| | | |
|---|---|---|
| EP | 0852674 | 12/2003 |
| WO | 2009067834 | 6/2009 |

* cited by examiner

*Primary Examiner* — Jill Warden
*Assistant Examiner* — Brittany Fisher
(74) *Attorney, Agent, or Firm* — Dykema Gossett PLLC

(57) ABSTRACT

The invention relates to a pipetting arrangement comprising at least two sets of pipettes (9a; 9b; 9c; 9d). Each set of pipettes (9a; 9b; 9c; 9d) is operationally connected, via a controllable ON/OFF valve (11a; 11b; 11e; 11d) to a common aspiration port (7). Latter is connectable to a pumping arrangement (3). The valves (11a; 11b; 11e; 11d) are controlled by a timing-control unit (15) conceived to establish, by control of the valves (11a; 11b; 11e; 11d), the operational connections of the at least two sets of pipettes (9a; 9b; 9c; 9d) to the aspiration port (7) in a time-multiplexed manner.

10 Claims, 4 Drawing Sheets

PIPETTING ARRANGEMENT AND METHOD OF CONTROLLING A PIPETTING ARRANGEMENT OR OF PRODUCING LIQUID PRODUCT DOSES

BACKGROUND OF THE INVENTION

1. Field of the Invention

The present invention relates to the field of preparing and handling of doses of liquids, thereby of very small doses down to e.g., some hundreds of nano-liters with accurately predetermined volumes. Such liquid handling techniques are especially used in context with medical, chemical or biochemical analyses, e.g., in pharmaceutical, medical or food industry laboratories.

2. The Prior Art

Thereby, it is of utmost importance to aspire, as probes e.g. to be analyzed, small samples of liquids of accurately known volumes and often at a high rate. Latter may be important e.g. in context with blood analyses of large populations, as become necessary to rapidly track out-braking contagious illnesses.

It is known to aspirate liquids from multiple receptacles by pipettes. The pipettes are thereby conveyed to and aligned with receptacles, lowered so as to be dipped in the respective liquids in the receptacles. To each pipette there is associated a valve- and a pumping-arrangement. By respective control of the valves and of the pumping arrangements, each pipette aspirates the respective dose of liquid from the receptacle. So as to ascertain that the volumes of the aspirated doses—the samples—accurately accord with the predetermined, rated volumes, with deviations of only few percentages, high demands must be fulfilled by the pumping arrangement, by the valves and by the respective controls.

We understand under a "rated" volume of a dose, the volume of a dose which is desired. A dose as produced should, ideally, have a volume equal to the rated volume.

The doses of liquids once aspirated into the pipettes are customarily conveyed within the pipettes to a destination location where they are released from the pipettes by respective controls of the valves and pumping arrangements.

Subsequently the pipettes can be rinsed with a rinsing solution, if necessary.

The aspiration steps are performed in that all valves and pumping arrangements, each associated to one pipette, are operated simultaneously or staggered in time.

It is an object of the present invention to provide an alternative pipetting arrangement and an alternative method of controlling a pipetting arrangement or of producing liquid product doses.

SUMMARY OF THE INVENTION

This is achieved according to the present invention by a pipetting arrangement which comprises at least two sets of pipettes. Each set of pipettes is operationally connected via a controllable ON/OFF-(open/closed) valve to a common aspiration port. The aspiration port is connectable to a pumping arrangement. The valves are controlled by a timing-control unit. The timing-control unit is conceived to establish, by the control of the valves, the respective operational connections of the at least two sets of pipettes to the aspiration port in a time-multiplexed manner.

Thus there is exploited, commonly for the at least two sets of pipettes, one pumping arrangement. Such pumping arrangement may be a remote pumping- or evacuation-station which feeds a line-network in a building installation, may be a pump arrangement centralized for a number of different equipments, or a distinct pump arrangement for the pipetting arrangement, integrated to or remote from a liquid handling device which comprises the addressed pipetting arrangement.

We understand throughout the present description and claims under "a pipette" a tubular member with one opening for aspiration and release of a liquid product dose and with a second opening whereat aspirating vacuum is controllably applied.

We further understand throughout the present description and claims under a "set of pipettes" one or more than one pipette having one common opening for applying aspirating vacuum. Thus, if such a set comprises more than one pipette, at one end of all pipettes their openings are in open communication. Obviously the pipettes of a set are operated in parallel, aspirating vacuum is applied to and removed from such pipettes simultaneously.

According to the present invention, for aspirating the respective doses one set of pipettes after the other is operationally connected to the common aspiration port which is operatively connected to a common pumping arrangement.

The number of highly sophisticated precision pumps as customarily assigned to each set of pipettes is drastically reduced. If e.g. a customary pipetting arrangement with ten sets of pipettes necessitates ten pumping arrangements, a pipetting arrangement according to the present invention necessitates just one pumping arrangement.

Thereby the constructional volume and weight of the pipette arrangement is significantly reduced.

Thus, the multiplexing technique according to the present invention has significant advantages over parallel aspiration techniques, e.g. with respect to constructional efforts, price, constructional volume and weight. Latter is especially important if one keeps in mind, that the overall pipetting arrangement is often moved at high accelerations from a seizing location to a destination location and back. By the reduction of weight of the pipetting arrangement with integrated single pumping arrangement it becomes possible to apply higher conveyance accelerations and/or to reduce driving forces the conveyor system has to stand and thus to optimize subsequent processing steps of liquid dose handling.

As was already addressed it is important to aspirate doses, the volume of which being as accurately as possible equal to respective rated volumes.

Time-multiplexing according to the present invention under its most generic aspect, associates to each set of pipettes a well defined time slot, during which such set is operationally connected to the aspiration port of or to a common pumping arrangement. The extent of these time slots is most accurately controllable and most accurately variable. The time-multiplexing technique according to the present invention, which exploits a single pumping arrangement for serving the at least two or more sets of pipettes, allows utmost flexibility to serve all sets in multiplexing mode, to serve two or more sets simultaneously and thus in parallel, to group the sets in groups of sets which are served in parallel and time multiplexed with other groups etc.

In one embodiment of the invention which may be combined with any other embodiment of the invention unless in contradiction, at least one of the at least two sets of pipettes comprises one single pipette.

In one other embodiment of the invention, which may be combined with any other embodiment of the invention unless in contradiction, the pipette arrangement comprises the common pumping arrangement operationally connected to the aspiration port. In this embodiment the pumping arrangement is part of the pipetting arrangement according to the invention.

In one embodiment thereof, such pumping arrangement comprises a gear pump, preferably an annular gear pump, as described e.g. in the EP 0 852 674 B1. This leads to a very accurately operating and highly compact pipetting arrangement.

In one other embodiment of the invention, which may be combined with any other embodiment of the invention unless in contradiction, the timing-control unit which in fact establishes for time-multiplexing, is controllable to alternatively and selectably establish the operational connections of the at least two set of pipettes to the aspiration port simultaneously. Thus, flexibly, one may select to serve the sets of pipettes in time multiplexed mode or in parallel.

In one other embodiment of the invention, which may be combined with any other embodiment of the invention unless in contradiction, the pumping arrangement is controlled to be ongoingly operative during establishing, by control of the valves, the operational connections of the at least two sets to the aspiration port in a time-multiplexed manner. This avoids switching the pumping arrangement on and off. In this embodiment the volumes of the aspirated doses is merely defined by the controlled operation of the valves, i.e. the time spans during which the respective valves are open.

In an alternative embodiment of the invention which may be combined with any other embodiment of the invention unless in contradiction, the pumping arrangement is controlled to be intermittently operated in an ON and in an OFF mode, synchronized with establishing, by control of the valves, the operational connections of the at least two sets of pipettes to the aspiration port in a time-multiplexed manner. In this embodiment, which is today preferred, the volumes of the doses as aspired are merely defined by the power of the pumping arrangement and the respective time spans the pumping arrangement is operating.

In another embodiment of the invention which may be combined with any other embodiment of the invention unless in contradiction, the valves are tailored to eject or to aspirate a volume which is neglectable when controlled from OFF to ON state or inversely. Thereby accuracy of the aspirated volumes becomes influenced by operation of the valves only to a neglectable amount.

In an other embodiment of the invention, which may be combined with any other embodiment of the invention unless in contradiction,a flow sensor is provided in a common line from the pumping arrangement to the sets of pipettes. Thereby it becomes possible to monitor with a single flow sensor the flow towards the pumping arrangement, e.g. indicating that one of the pipettes or is blocked.

A liquid handling device according to the invention, which comprises a pipetting arrangement according to the invention in one or more than one of its specific embodiments, is highly cost effective, exhibits a small volumed and small weighted pipetting arrangement and is most flexibly controllable.

One embodiment of the liquid handling device according to the invention, which may be combined with any other embodiment of such device unless in contradiction, comprises a controlled positioning drive controlling position of the pipetting arrangement along at least two spatial coordinate axes. Thereby the pipetting arrangement is drivingly positioned in respective positions e.g. as defined in an x/y coordinate system.

In one further embodiment of the liquid handling device according to the invention, which may be combined with any other embodiment of such device, unless in contradiction, the controlled positioning drive controls position of the pipetting arrangement and/or of the two sets in a mutually independent manner, along a third spatial coordinate axis.

It is also possible to move and position the sets mutually independently in all three or only in two coordinate directions.

Thereby the pipetting arrangement becomes drivingly positionable e.g. with respect to a z coordinate and/or the sets of pipettes become individually and independently positionable with respect to the addressed third spatial coordinate.

A further object of the present invention is to improve control of a pipetting arrangement or to improve production of liquid doses of predetermined volumes. This is achieved by a method of controlling a pipetting arrangement or of producing at least two liquid doses of predetermined volumes, which comprises, dipping a first of at least two sets of pipettes into a first reservoir containing a first liquid, operationally connecting the first set of pipettes to an aspiration port operationally connected to a pumping arrangement and establishing an aspirating effect at said aspiration port, thereby aspirating first liquid into the first set of pipettes;

closing a first ON/OFF valve interconnected between said first set of pipettes and said aspiration port;

dipping a second set of the at least two sets of pipettes into a second reservoir containing a second liquid, operationally connecting the second set of pipettes to the aspiration port operationally connected to the pumping arrangement and establishing an aspirating effect at the aspiration port, thereby aspirating second liquid into the second set of pipettes;

closing a second ON/OFF valve interconnected between the second set of pipettes and the aspiration port;

thereby time multiplexing said operational connections from the first set of pipettes and from the second set of pipettes to the aspiration port by respectively time-controlled opening of the first and second ON/OFF valves.

Thereby, it becomes possible to perform dose-producing with reduced hardware efforts, leading to an overall reduction of price per handled liquid dose and even to higher throughput of handled doses.

In one embodiment of the method according to the invention, which may be combined with any embodiment of such method unless in contradiction, at least one of the at least two sets of pipettes is selected to comprise one single pipette.

In one embodiment of the method according to the invention, which may be combined with any embodiment of such method unless in contradiction, the aspirating effect is kept ongoing during multiplexing.

In one embodiment of the method according to the invention, which may be combined with any embodiment of such method unless in contradiction, the aspirating effect at said aspiration port is intermittently established, synchronised with the multiplexing.

In one embodiment of the method according to the invention, which may be combined with any embodiment of such method, unless in contradiction, there is valid at least one of:
the first and the second liquids are different,
the first and the second receptacles are two distinct receptacles,
the dippings of the first and of the second sets of pipettes is performed simultaneously.

In one embodiment of the method according to the invention, which may be combined with any embodiment of such method unless in contradiction, there is provided an additional, selectable mode of operation, wherein the operational connections of the first and second sets of pipettes to the aspiration port are simultaneously established.

BRIEF DESCRIPTION OF THE DRAWINGS

The present invention shall further be exemplified with the help of figures. The figures show.

DETAILED DESCRIPTION OF THE DRAWINGS

Figure 1:
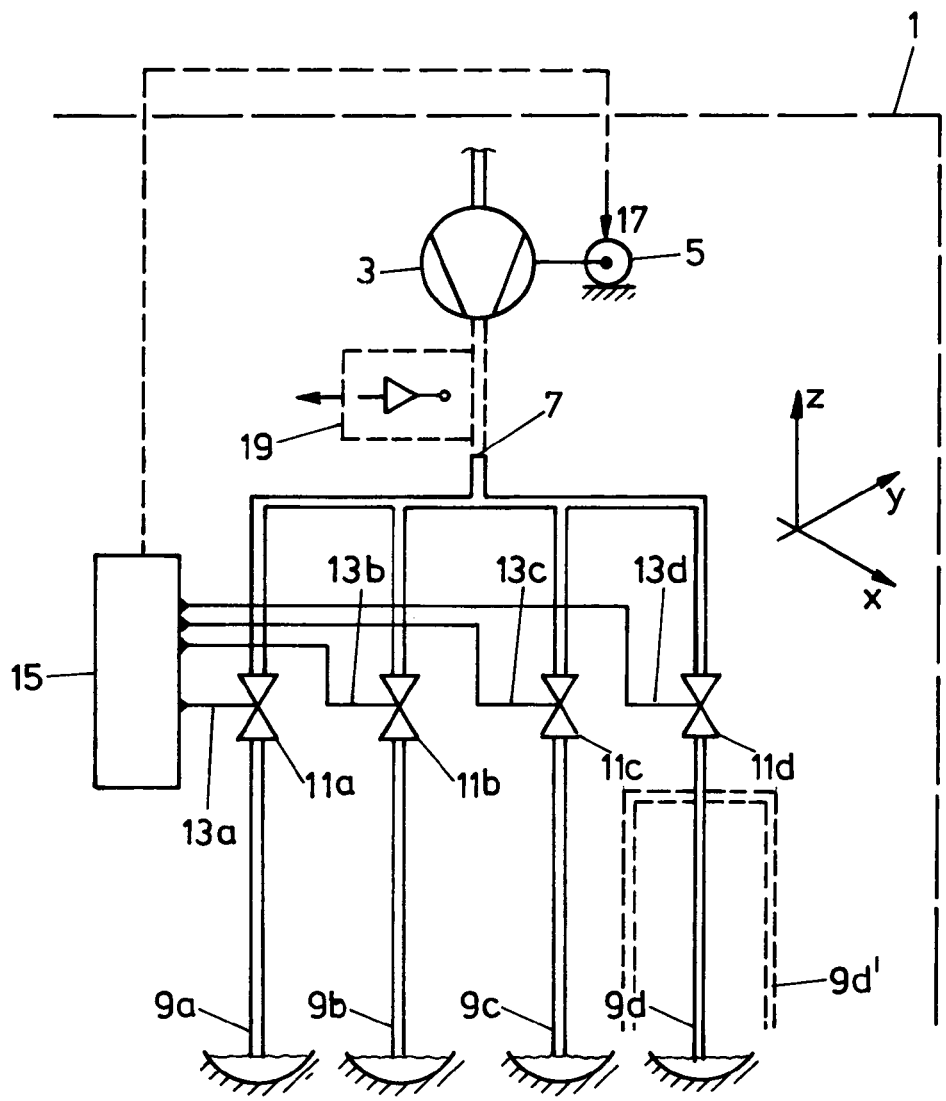
FIG. 1 schematically and simplified an embodiment of a pipetting arrangement according to the present invention, operated according to the method for producing or of controlling according to the invention.

FIG. 1 schematically shows an embodiment of a pipetting arrangement 1 according to the present invention. A pumping arrangement, exemplified in the figure by a pump 3 with a drive motor 5 is operationally connected to an aspiration port 7. As addressed by the dash line, the pumping arrangement may be remote from aspiration port 7 and thus from the pipetting arrangement, may be realised e.g. by a central pumping station of a laboratory building feeding a vacuum line network throughout such building. Nevertheless in a today realized embodiment the pumping arrangement is integral with the pipetting arrangement and comprises a pump 3. The aspiration port 7 is operationally connected to at least two, as exemplified to four sets of pipettes 9a, 9b, 9c and 9d via respective ON/OFF valves 11a, 11b, 11c, 11d, each being ON/OFF controlled by ON/OFF control signals applied to control inputs 13a, 13b, 13c, 13d. The valves may be pneumatically controlled or electrically which latter is the case in today's realized embodiment. The sets of pipettes may comprise one single pipette as represented in the figure, all of them or selected sets may nevertheless be realized by more than one pipette operated in parallel, as exemplified at 9d' in dash line.

If we speak throughout the present description and claims from a valve being "OFF" we mean the valve is "closed".

If we speak throughout the present description and claims from a valve being "ON" we mean the valve is "open".

The ON/Off control signals for the valves 11a to 11d are generated and timed by a timing-control unit 15.

ON/OFF operation of pump 3 is controlled by a control signal to the drive motor control input 17. The control signal to control input 17 is e.g. generated by the timing-control unit 15 as well.

Figure 2:
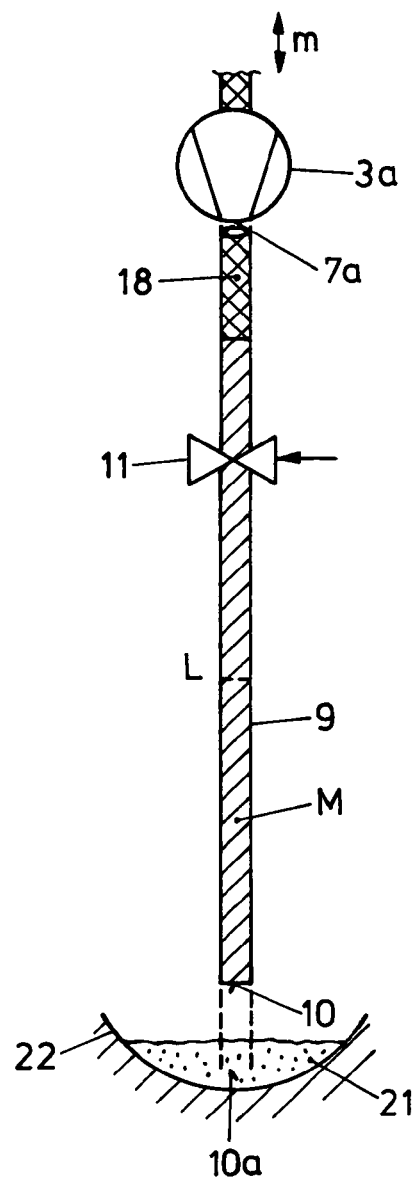
FIG. 2 in a representation in analogy to that of FIG. 1, a single pipette/valve/pump arrangement as of prior art, to explain the technique of aspirating of a dose of liquid, as principally also exploited according to present invention although with a different approach of realization.

Known operation of pipetting shall now be explained with the help of FIG. 2 to facilitate understanding of the present invention.

A pipette 9 is operationally connected to a pumping arrangement, as to a pump 3a via an ON/OFF valve 11. The pump 3a on one hand is permanently filled with a liquid medium which is conveyed forth and back by respective operation of the pump 3a as schematically shown by double arrow m. The system of pipette 9 and commonly also of valve 11 is filled with a gaseous or liquid medium M, we call this liquid "transmitter medium".

First the valve 11 is OFF, i.e. closed and thereby prevents any escape of liquid transmitter medium M from pipette 9, which customarily is vertically oriented. The bottom level of liquid transmitter medium M in the pipette 9 is at a predetermined position at or adjacent to the mouth 10 of the pipette.

The mouth 10 of pipette 9 is then immersed into a liquid 21 to be aspired as shown in dash line in FIG. 2 at 10a. We call this liquid the "dose liquid".

The pump 3a is started and simultaneously valve 11 is controlled into ON state, i.e. open state. The aspiration effect at the aspiration port 7a to pump 7 is transmitted by the transmitter medium M, irrespective whether liquid or gaseous, to the mouth 10a of the pipette: Dose liquid 21 is aspired into pipette 9.

As soon as a predetermined volume of dose liquid 21 is in the pipette 9 valve 11 is closed. The arrangement customary comprising pipette 9, valve 11 and pump 3a is lifted, so that the mouth 10 of pipette is freed from the remaining dosing liquid 21 in a receptacle 22.

With the valve kept close, the arrangement with the pipette 9 containing the dose of dosing liquid 21 e.g. up to a level L as indicated in FIG. 2 may now be conveyed as desired in a respective application.

Different techniques exist to accurately determine the level L and thereby, at a predetermined cross-section of the interior tube-space of the pipette 9, the volume of dose liquid 21 having been aspired in the pipette 9. Such techniques may for instance be based on light-barrier level detection as perfectly known to the skilled artisan.

Simultaneously with turning valve 11 in OFF (closed) state or shortly before or afterwards, pump 3a is customarily stopped or, more generically an aspirating effect to the pipette is disabled.

For releasing the dose of dosing liquid from pipette 9 into a destination receptacle (not shown), valve 9 is switched ON (open). E.g. the pump 3a is inversed in operation, and thus actively ejects the dose of liquid 21 into the destination receptacle. Here too different techniques are known to accurately control that exactly the same dose volume of liquid 21 is ejected into the destination receptacle as has been seized from the "source" recipient 22. Important to note, that in such prior art technique technique one pumping arrangement is dedicated to each pipette or set of pipettes.

After having explained the known generic technique of pipetting in automated liquid handling art in context with FIG. 2, let's turn back to the invention as represented in FIG. 1.

Here one common pumping arrangement, as of pump 3 is provided to serve more than one, as exemplified, four sets of pipettes 9a to 9d. This is done by time-multiplexing the aspiration effect at the aspiration port 7 from pump 3 consecutively to one set of pipettes after the other. Thereby the order of such sequence may be selected as desired, for clearness sake, multiplexing of the aspiration effect shall be from 9a to 9b to 9c to 9d in FIG. 1.

With respect to provision of the media m and M the same prevails as was described in context with FIG. 2.

Figure 3:
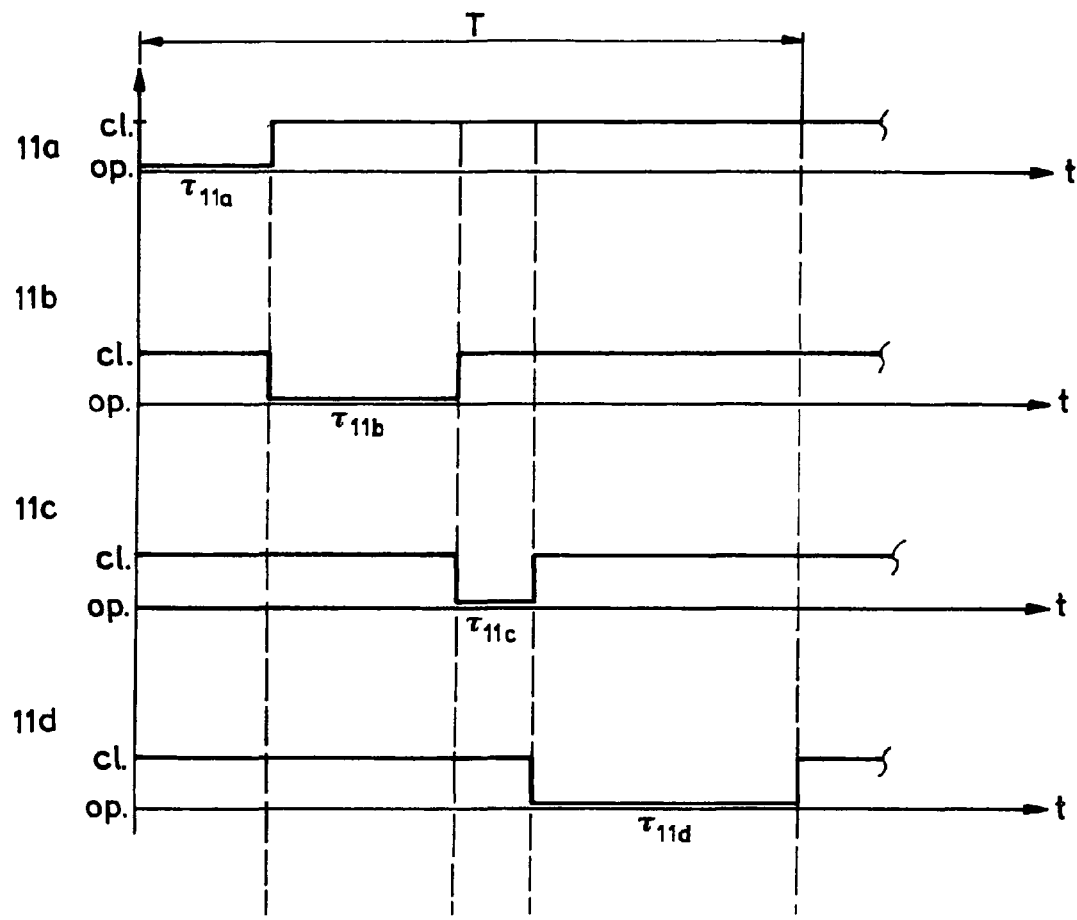
FIG. 3 qualitatively, a timing diagram of the control of the valves as incorporated in the embodiment of FIG. 1.

FIG. 3 qualitatively shows the timing diagram of the multiplexing control of the valves 11a to 11d by the control signals generated by control unit 15 and applied to control inputs 13a to 13d of the respective valves. In FIG. 3 "cl." addresses "close" (OFF State) and "op." addresses "open" (ON state) of the respective valves. Further $\tau_{11a}$ to $\tau_{11d}$ address the respective time slots a respective valve 11a to 11d is open. T is the overall cycle time to fill all the four sets of pipettes.

Thus with an eye on FIG. 3, first valve 11a is opened during time slot $\tau_{11a}$. At the end of $\tau_{11a}$ valve 11a is closed and at least substantially simultaneously, possibly with a small time lag, valve 11b is opened for the time slot $\tau_{11b}$. In perfect analogy to multiplexing the sets of pipettes 9a and 9b as just described to the aspiration effect at aspiration port 7 of pump 3, subsequently, the sets of pipettes 9c and then 9d are multiplexed to the aspiration effect at port 7 during respective time slots $\tau_{11c}$, $\tau_{11d}$.

Thus it becomes apparent that one time slot is associated to every pipette.

The extents and the time sequence of the time slots is freely selectable. Further and if desired it is absolutely possible to flexibly establish two or more of the time slots to occur simultaneously or overlappingly and thereby to operate respectively selected sets—if desired even all sets—simultaneously and thus in parallel. Still further and if desired one set considered may be operated during more than one time slot. This e.g. if a fixed time slot duration for all sets is established, in the sense of a system clock, and doses of different volumes are to be aspirated at different sets of pipettes.

There is aspirated into each set of pipettes a dose with a volume which is proportional to the time slot duration the addressed set is operationally connected to the common aspiration port 7. In today's realization form which has proven most accurate, a gear pump, preferably an annular gear pump as described e.g. in the EP 0 852 674 B1 is integrated to the pipetting arrangement thereby forming with the addressed arrangement a commonly moved and positioned unit.

Clearly ejecting accurately the same doses as aspirated at the destination is performed by opening the respective valve and inversely operating the pump exactly during the respective duration according to $\tau_{11x}$.

As exemplified in FIG. 3, the extents of the multiplexing time slots $\tau_{11x}$ may be selected to be equal or, as shown, different. Thereby by means of controlling the extents of these time slots $\tau_{11x}$ the volume of each aspirated dose may be separately selected.

Although it may be possible to operate pump 3 ongoingly during cycle time T and thereby performing multiplexing the aspiration effect merely by ON/OFF control of the valves 11a to 11d, it is today preferred to operate the pump 3 intermittently, synchronized with multiplexing.

Figure 4:
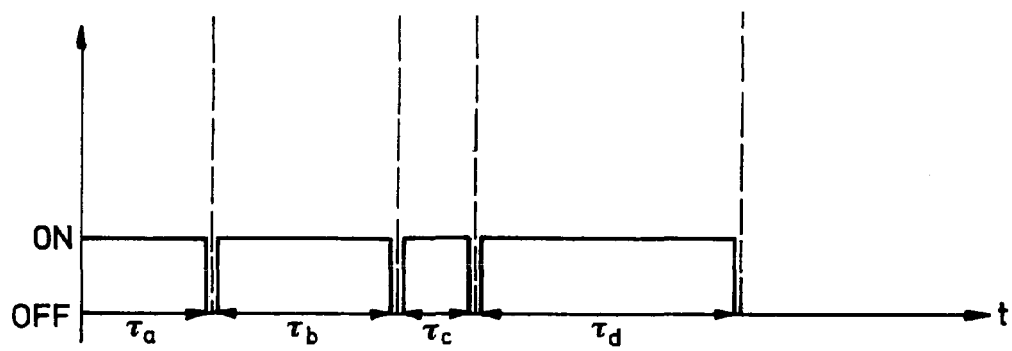
FIG. 4 qualitatively, a timing diagram, to be considered in context with FIG. 3, of intermittent pump operation, synchronized with occurrence of time slots as of FIG. 3, as one form of realization of the invention.

FIG. 4 shows, associated with FIG. 3, a timing diagram of such intermittent pump operation. Here the respective ON times $\tau_a$ to $\tau_d$ of the pump control the respectively aspirated volumes of the doses, whereas the valves 11a to 11d control time multiplexing and accurate retention of the aspirated dosing liquid within the sets of pipettes.

The valves 11a to 11d should propel a vanishing volume of transmitter medium M (see FIG. 2) in the transients ON to OFF and OFF to ON, so as not to falsify the aspirated volume of the respective doses controlled on one hand by the operation state of the pump and, on the other hand, by the respective time spans $\tau_a$ to $\tau_d$.

So as to monitor proper functioning of the pipette arrangement, it might be advisable to provide a flow sensor arrangement in the common line from the sets of pipettes to the pumping arrangement. Such flow sensor is shown in FIG. 1 in dash line and by reference number 19. By monitoring the flow by means of a single flow sensor at the addressed one location it becomes possible to detect a failing aspiration in any of the time-multiplexed sets of pipettes.

Figure 5:
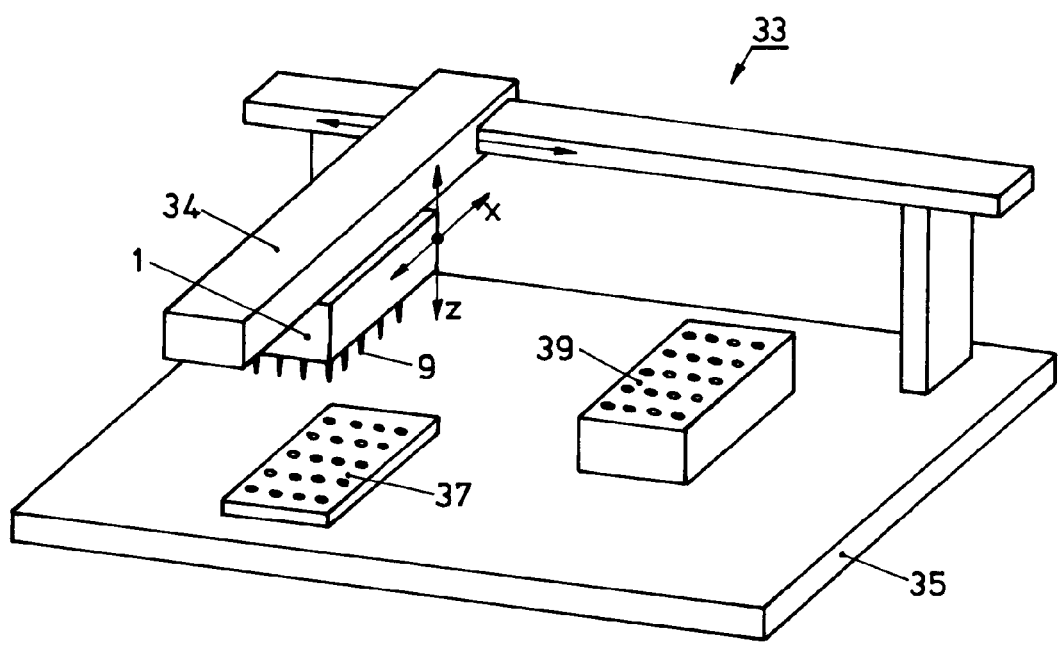
FIG. 5 schematically and simplified, a liquid sample processing device according to the invention and comprising a pipetting arrangement according to the invention.

FIG. 5 schematically shows a liquid handling apparatus or device 33 with a pipetting arrangement 1 according to the present invention integrated in a conveyor arm 34. The conveyor arm 34 provides for driven movability of the pipettes 9 in x- and z-direction as is schematically shown in FIG. 1 with respect to an apparatus frame 35. The arm 34 itself is drivingly movable in y-direction with respect to the frame 35. The valves 11 as well as pump 3 are integrated in the arrangement 1.

The sets of pipettes 9 can be dipped by controlled movement in z-direction into sample receptacles 37 with the respective dose liquids. The aspirated doses are then conveyed in x and y direction to destination receptacles 39. Thereby in one embodiment all the sets of pipettes are commonly driven and positioned in z-direction, in an other embodiment (not shown) distinct sets or groups of sets may be driven and positioned in z direction mutually independently.

We understand in context with the present description and claims under a "device comprising the pipetting arrangement", and with an eye on FIG. 5, e.g. the overall apparatus or the arm 34 or the arm with the frame, in other words all parts at which a pipetting arrangement is provided up to the complete apparatus.

By the present invention under all its aspects, a significant reduction of hardware effort for multiple pipette liquid handling is achieved.

The invention claimed is:

1. A method of controlling a pipetting arrangement or of producing at least two liquid doses of predetermined volumes, comprising:
    dipping a first of at least two sets of pipettes into a first reservoir containing a first liquid, operationally connecting, via a gaseous transmitter medium, said first set of pipettes to an aspiration port operationally connected to a pumping arrangement and establishing an aspirating effect at said aspiration port;
    opening a first ON/OFF valve in said gaseous transmitter medium, and interconnected between said first set of pipettes and said aspiration port, thereby aspirating first liquid into said first set of pipettes;
    closing said first ON/OFF valve in said gaseous transmitter medium and interconnected between said first set of pipettes and said aspiration port;
    dipping a second set of said at least two sets of pipettes into a second reservoir containing a second liquid, operationally connecting via said gaseous transmitter medium, said second set of pipettes to said aspiration port operationally connected to said pumping arrangement and establishing an aspirating effect at said aspiration port;
    opening a second ON/OFF valve in said gaseous transmitter medium, and interconnected between said second set of pipettes and said aspiration port, thereby aspirating second liquid into said second set of pipettes;
    closing said second ON/OFF valve in said gaseous transmitter medium and interconnected between said second set of pipettes and said aspiration port;
    thereby time-multiplexing said operational connections from said first set of pipettes and from said second set of pipettes to said aspiration port by respectively time-controlled opening of said first and second ON/OFF valves;
    said pumping arrangement being controlled to be ongoingly operative during said multiplexing, and
    establishing the volumes of said aspirated doses merely by selecting the time spans during which said valves are respectively open.

2. The method of claim 1, comprising selecting at least one of said at least two sets of pipettes to comprise one single pipette.

3. The method of claim 1, comprising at least one of:
said first and second liquids being different,
said first and second receptacles being two distinct receptacles,
said dippings being performed simultaneously.

4. The method of claim 1, further comprising an additional, selectable mode of operation, wherein said operational connections of said first and second sets of pipettes to said aspiration port are simultaneously established.

5. The method of claim 1, wherein said pumping arrangement comprises a line network and a pressurizing station in a building installation.

6. A method of controlling a pipetting arrangement or of producing at least two liquid doses of predetermined volumes, comprising:
applying a first of at least two sets of pipettes to a first reservoir for a first liquid, operationally connecting, via a gaseous transmitter medium, said first set of pipettes to a pressure port operationally connected to a pumping arrangement and establishing an ejecting effect at said pressure port;
opening a first ON/OFF valve in said gaseous transmitter medium, and interconnected between said first set of pipettes and said pressure port, thereby ejecting first liquid from said first set of pipettes;
closing said first ON/OFF valve in said gaseous transmitter medium and interconnected between said first set of pipettes and said pressure port;
applying a second set of said at least two sets of pipettes to a second reservoir for a second liquid, operationally connecting, via said gaseous transmitter medium, said second set of pipettes to said pressure port operationally connected to said pumping arrangement and establishing an ejecting effect at said pumping port;
opening a second ON/OFF valve in said gaseous transmitter medium and interconnected between said second set of pipettes and said pressure port, thereby ejecting second liquid from said second set of pipettes;
closing said second ON/OFF valve in said gaseous transmitter medium and interconnected between said second set of pipettes and said pressure port;
thereby time-multiplexing said operational connections from said first set of pipettes and from said second set of pipettes to said pressure port by respectively time-controlled opening of said first and second ON/OFF valves;
said pumping arrangement being controlled to be ongoingly operative during said multiplexing, and establishing the volumes of said ejected doses merely by selecting the time spans during which said valves are respectively open.

7. The method of claim 6, comprising selecting at least one of said at least two sets of pipettes to comprise one single pipette.

8. The method of claim 6, comprising at least one of:
said first and second liquids being different,
said first and second receptacles being two distinct receptacles,
said dippings being performed simultaneously.

9. the method of claim 6, further comprising an additional, selectable mode of operation, wherein said operational connections of said first and second sets of pipettes to said aspiration port are simultaneously established.

10. The method of claim 6, wherein said pumping arrangement comprises a line network and a pressurizing station in a building installation.

\* \* \* \* \*